US011529419B2

(12) United States Patent
Lemieux et al.

(10) Patent No.: US 11,529,419 B2
(45) Date of Patent: *Dec. 20, 2022

(54) STARCH-BASED RELEASE MODIFYING EXCIPIENTS AND PHARMACEUTICAL COMPOSITIONS DERIVED THEREFROM

(71) Applicant: ALTUS FORMULATION INC., Mirabel (CA)

(72) Inventors: Marc Lemieux, Mascouche (CA); Bradut Mitrasca, Laval (CA); Sonia Gervais, Laval (CA); Damon Smith, Ville Saint Laurent (CA)

(73) Assignee: ALTUS FORMULATION INC., Mirabel (CA)

( * ) Notice: Subject to any disclaimer, the term of this patent is extended or adjusted under 35 U.S.C. 154(b) by 6 days.

This patent is subject to a terminal disclaimer.

(21) Appl. No.: 17/345,462

(22) Filed: Jun. 11, 2021

(65) Prior Publication Data

US 2021/0299259 A1 Sep. 30, 2021

Related U.S. Application Data

(63) Continuation of application No. 16/477,028, filed as application No. PCT/CA2018/051279 on Oct. 11, 2018, now Pat. No. 11,058,773.

(60) Provisional application No. 62/572,037, filed on Oct. 13, 2017.

(30) Foreign Application Priority Data

Oct. 16, 2017 (GB) ..................... 1716965

(51) Int. Cl.
| | | |
|---|---|---|
| A61K 47/38 | (2006.01) | |
| A61K 31/138 | (2006.01) | |
| A61K 31/167 | (2006.01) | |
| A61K 31/415 | (2006.01) | |
| A61K 31/496 | (2006.01) | |
| A61K 9/24 | (2006.01) | |

(52) U.S. Cl.
CPC .......... *A61K 47/38* (2013.01); *A61K 31/138* (2013.01); *A61K 31/167* (2013.01); *A61K 31/415* (2013.01); *A61K 31/496* (2013.01); *A61K 9/209* (2013.01)

(58) Field of Classification Search
None
See application file for complete search history.

(56) References Cited

U.S. PATENT DOCUMENTS

| | | |
|---|---|---|
| 5,807,575 A | 9/1998 | Dumoulin et al. |
| 6,184,213 B1 | 2/2001 | Lefevre et al. |
| 6,607,748 B1 | 8/2003 | Lenaerts et al. |
| 8,414,919 B2 | 4/2013 | Gervais et al. |
| 2009/0285863 A1* | 11/2009 | Podczeck ............. A61K 9/5047 514/6.9 |
| 2010/0104638 A1 | 4/2010 | Dai et al. |

FOREIGN PATENT DOCUMENTS

| | | |
|---|---|---|
| WO | 9943305 A1 | 9/1999 |
| WO | 2004064544 A1 | 8/2004 |
| WO | 2007048220 A2 | 5/2007 |
| WO | 2009049405 A1 | 4/2009 |
| WO | 2009076764 A1 | 6/2009 |
| WO | 2010028489 A1 | 3/2010 |

OTHER PUBLICATIONS

Onfre et al. "Sustained release properties of cross-linked corn starches with varying amylose contents in monolithic tablets" 2010.*
Bhardway et al., "Natural Gums and Modified Natural Gums as Sustained-Release Carriers," Drug Development and Industrial Pharmacy, 2000, vol. 26 (10), pp. 1025-1038.
Devane C., "Immediate-release Versus Controlled-Release Formulations: Pharmacokinetics of Newer Antidepressants in Relation to Nausea," The Journal of Clinical Psychiatry, 2003, vol. 64 Suppl. 18, pp. 14-19.
Drugs.com., "Acetaminophen Dosage," Last updated on Feb. 28, 2020, 9 pages. Retrieved from Internet:[URL: https://www.drugs.com/dosage/acetaminophen.html].
European Patent Application No. 18867198.6, Extended European Search Report dated May 21, 2021.
Hiremath et al., "Controlled Release Hydrophilic Matrix Tablet Formulations of Isoniazid: Design and in Vitro Studies," AAPS PharmSci Tech, 2008, vol. 9 (4), pp. 1171-1178.
International Patent Application No. PCT/CA2018/051279, International Search Report and Written Opinion dated Jan. 24, 2019.
International Preliminary Report on Patentability in International Application No. PCT/CA2018/051279, dated Apr. 14, 2020.
Klein., "The Role of Extended-release Benzodiazepines in the Treatment of Anxiety: a Risk-benefit Evaluation With a Focus on Extended-release Alprazolam," The Journal of Clinical Psychiatry, Feb. 2002, vol. 63 Suppl 14(Suppl 14), pp. 27-33.

(Continued)

*Primary Examiner* — Danah Al-Awadi
(74) *Attorney, Agent, or Firm* — Borden Ladner Gervais LLP; Graeme R. B. Boocock

(57) ABSTRACT

There is provide an extended release dosage form comprising a release modifying excipient comprising high amylose starch, cross-linked hydroxypropylated amylopectin, and a pre-gelatinized common starch; wherein the release modifying excipient is substantially free of crosslinks between amylose and amylopectin and substantially free of crosslinks between amylose and amylose. It has been found that the extended release properties of conventional cross-linked high amylose starches (e.g., Contramid®) can be reproduced by intimately mixing i) cross-linked chemically modified amylopectin; ii) a high amylose, non-chemically modified starch and; iii) a pre-gelatinized common starch. Producing a release modifying excipient in this way means that no chemical cross linking between (a) amylose and amylopectin or (b) amylose and amylose has occurred—properties heretofore considered vital for Contramid® function. The release modifying excipient blends overcome problems associated with use of Contramid, and provide a flexible platform for formulation of active pharmaceutical ingredients for controlled release applications.

16 Claims, 8 Drawing Sheets

(56) References Cited

OTHER PUBLICATIONS

Michelson., "Calcium Antagonists in Cardiology: Update on Sustained-Release Drug Delivery Systems," Clinical Cardiology, Dec. 1991, vol. 14 (12), pp. 947-950.
Moore et al., "Mathematical Comparison of Dissolution Profiles," Pharmaceutical Technology, 1996, vol. 20 (6), pp. 64-74.
Navarro., "Improving Medication Compliance in Patients With Depression: Use of Orodispersible Tablets," Advances in Therapy, Nov. 2010, vol. 27 (11), pp. 785-795.
Nicholson., "Benefits of Extended-Release Opioid Analgesic Formulations in the Treatment of Chronic Pain," Pain practice, Jan.-Feb. 2009, vol. 9 (1), pp. 71-81.
Onofre F.O., et al., "Sustained Release Properties of Cross-linked Corn Starches With Varying Amylose Contents in Monolithic Tablets," Starch vol. 62 (3-4), pp. 165-172, 2010.
Porter., "Controlled-Release Film Coatings Based on Ethylcellulose," Drug Development and Industrial Pharmacy, 1989, vol. 15 (10), pp. 1495-1521.
Rosiaux et al., "Ethanol-resistant Polymeric Film Coatings for Controlled Drug Delivery," Journal of Control Release, Jul. 2013, vol. 169 (1-2), pp. 1-9.
Singh et al., "Osmotic Pump Drug Delivery System: A Noval Approach," Journal of Drug Delivery & Therapeutics, 2013, vol. 3 (5), pp. 156-162.
Thakral et al., "Eudragit®: A Technology Evaluation," Expert Opinion on Drug Delivery, 2013, vol. 10 (1), pp. 131-149.
Ultram., "Tramadol hydrochloride Tablets," Full Prescribing information, 22 pages. Retrieved from Internet:[URL: https://www.accessdata.fda.gov/drugsatfda_docs/label/2009/020281s032s033lbl.pdf].
United Kingdom Patent Application No. 1716965.7, Search Report dated Jun. 27, 2018.
United States U.S. Appl. No. 16/477,028, Non-Final Office Action dated Nov. 17, 2020.
United States U.S. Appl. No. 16/477,028, Notice of Allowance dated Mar. 10, 2021.

\* cited by examiner

STARCH-BASED RELEASE MODIFYING EXCIPIENTS AND PHARMACEUTICAL COMPOSITIONS DERIVED THEREFROM

RELATED APPLICATIONS

This application is a continuation of U.S. patent application Ser. No. 16/477,028, filed Jul. 10, 2019, which is a National Phase Entry of PCT/CA2018/051279 filed Oct. 11, 2018, which claims the benefit of priority of U.S. Provisional Application No. 62/572,037 entitled "STARCH-BASED RELEASE MODIFYING EXCIPIENTS AND PHARMACEUTICAL COMPOSITIONS DERIVED THEREFROM" and filed Oct. 13, 2017; and of UK Application No. 1716965 entitled "STARCH-BASED RELEASE MODIFYING EXCIPIENTS AND PHARMACEUTICAL COMPOSITIONS DERIVED THEREFROM" and filed Oct. 16, 2017. These applications are herein incorporated by reference in their entireties.

FIELD

The present disclosure relates generally to release modifying excipients for delivery of an active pharmaceutical ingredient (API). More particularly, the present disclosure relates to dosage forms comprising a starch-based release modifying excipient.

BACKGROUND

Conventional pharmaceutical dosage forms must often be taken four to six times per day if efficacy is to be maintained. Extended release pharmaceutical dosage forms (ER DFs) that must be taken only once or twice a day are valuable as they are more convenient for patients to use than conventional forms. While they can also reduce side effects, ER DFs also promote dosing compliance, i.e., the likelihood patients will remember to take their dosage forms on time.

ER DFs are valuable for delivery of almost all active pharmaceutical ingredients (API) but are especially beneficial for pain medications where failure to adhere to a dosing regimen can lead to breakthrough pain and, thereby, the chance that patients will overmedicate to compensate for missed doses. This can lead to dangerous adverse events. Similarly, ER DFs are highly valuable for CNS drugs such as antidepressants where it is well known that patients are poorly compliant, resulting in under medication and a recurrence of symptoms.

Starch-based excipient technology is used in the formulation of APIs for drug delivery to individuals in need thereof, and is especially useful for formulation of ER DFs. In particular, it is used in matrix type drug delivery systems wherein an API is blended with a modified starch excipient followed by compression into a dosage form.

Upon ingestion of the dosage form, the gelling properties of the starch-based excipients are thought to create a barrier to immediate release of the API in the gastrointestinal environment. Consequently, the period of time over which the API is released to enter the bloodstream is extended and the effects of the API are thereby prolonged.

Starch-based excipients for pharmaceutical use include cross-linked high amylose starches (CLHAS). These starches, comprising cross linked and chemically modified amylopectin and amylose subunits, are derived from high amylose starches (HAS) extracted from low-cost, high-abundance farm crops including corn, potato or pea crops. The gelling properties of CLHAS vary according to the HAS of the variety of plant from which they are is derived as well as natural variation within the plant species. HAS from corn varieties with very high amylopectin content (waxy starches) are known to generate more viscous gels when added to water than modified starches derived from low amylopectin varieties (common starches). HAS gel viscosity affects the release modifying properties of the derived CLHAS To date, only corn-derived HAS have been used to manufacture CLHAS for the development of ER DF on a commercial scale. To generate their release modifying properties these starches must first be chemically modified. Starch modification comprises two steps, namely, cross linking and side chain modification.

Cross linking is believed to add structural rigidity to the HAS and to limit over swelling in the presence of water. Crossing linking results in covalent bonding between the amylose and amylopectin, amylose and amylose and amylopectin and amylopectin subunits of the HAS. The starch side chains are then treated with modifying agents including propylene oxide, which introduces hydroxypropyl groups to a limited number of carbohydrate units on both amylose and amylopectin. This modification is intended to limit crystallinity and increase swelling. Finally, after additional washing steps, the cross-linked hydroxypropylated starch is washed, heat treated and then spray dried. It is well known that the functionality of the CLHAS produced by chemical modification can be highly dependent on the exact manufacturing process used. Examples of CLHAS that may be used in ER dosage forms are CLHAS developed by Rougier Inc. Canada and Labopharm Inc. Canada where the CLHAS is also known as Contramid®.

Although CLHAS are valuable for drug delivery, the technology remains challenging, for example due to one or more of: batch-to-batch inconsistency; an inability to optimize the amylose to amylopectin ratio; and limited supply.

First, because HAS is derived from natural sources, there is batch-to-batch inconsistency with seasonal and annual variations in the ratio of amylose to amylopectin. This can result in inconsistent gelling speeds between batches and therefore inconsistent effectiveness in pharmaceutical applications, particularly in large scale commercial production.

Second, the viscosity of HAS cannot be optimized for any particular API. While natural variation between corn varieties in the ratio of amylose to amylopectin can be exploited to enhance ER delivery, it is not currently possible to synthesize HAS containing an optimized ratio for any particular API on-demand or at a commercial scale.

Third, the number of suppliers of CLHAS for pharmaceutical applications is limited. Therefore, pharmaceutical compositions containing excipients for matrix systems for ER delivery are vulnerable to a single point of failure. This could have detrimental consequences for individuals relying on effective, long-acting formulations.

It is, therefore, desirable to provide an alternative to conventional CLHAS.

SUMMARY

It is an object of the present disclosure to obviate or mitigate at least one disadvantage of previous approaches.

In a first aspect, there is provided an extended release pharmaceutical dosage form comprising an active pharmaceutical ingredient (API) and a release modifying excipient, the release modifying excipient comprising: 35% to 95% (wt/wt) of a high amylose starch, 1% to 40% (wt/wt) of a cross-linked hydroxypropylated amylopectin, and 1% to 30% (wt/wt) of a pre-gelatinized common starch, wherein the release modifying excipient is substantially free of crosslinks between amylose and amylopectin subunits and substantially free of crosslinks between amylose and amylose subunits.

In another aspect, there is provided an extended release pharmaceutical dosage form comprising: tramadol or a pharmaceutically acceptable salt thereof and a release modifying excipient, the release modifying excipient comprising: 70-80% (wt/wt) of a high amylose starch, 10-20% (wt/wt) of a cross-linked hydroxypropylated amylopectin, and 5-15% (wt/wt) of a pre-gelatinized common starch, wherein the release modifying excipient is substantially free of crosslinks between amylose and amylopectin subunits and substantially free of crosslinks between amylose and amylose subunits.

In another aspect, there is provided an extended release pharmaceutical dosage form comprising: trazodone or a pharmaceutically acceptable salt thereof and a release modifying excipient, the release modifying excipient comprising: 70-80% (wt/wt) of a high amylose starch, 10-20% (wt/wt) of a cross-linked hydroxypropylated amylopectin, and 5-15% (wt/wt) of a pre-gelatinized common starch, wherein the release modifying excipient is substantially free of crosslinks between amylose and amylopectin subunits and substantially free of crosslinks between amylose and amylose subunits.

In another aspect, there is provided a bilayer extended release pharmaceutical dosage form comprising: an immediate release portion comprising acetaminophen, and a release controlling portion comprising acetaminophen and a release modifying excipient, the release modifying excipient comprising: 70-80% (wt/wt) of a high amylose starch, 10-20% (wt/wt) of a cross-linked hydroxypropylated amylopectin, and 5-15% (wt/wt) of a pre-gelatinized common starch, wherein the release modifying excipient is substantially free of crosslinks between amylose and amylopectin subunits and substantially free of crosslinks between amylose and amylose subunits.

In another aspect, there is provided a use of the extended release pharmaceutical dosage defined herein for delivery the API to a subject.

In another aspect, there is provided a method of delivering an API to a subject comprising administering to the subject the pharmaceutical dosage form as defined herein.

In another aspect, there is provided a method of optimizing a release controlling excipient for an active pharmaceutical ingredient (API), the method comprising: selecting a target release property for a dosage from comprising the API, selecting an amount of a high amylose starch, selecting an amount of a cross-linked hydroxypropylated amylopectin, and selecting an amount of a pre-gelatinized common starch, blending the high amylose starch, the cross-linked hydroxypropylated amylopectin, and the pre-gelatinized common starch using the selected amounts to form a release controlling excipient, wherein the release controlling excipient is substantially free of crosslinks between amylose and amylopectin subunits and substantially free of crosslinks between amylose and amylose subunits, forming a dosage form comprising the API and the release controlling excipient, and testing the dosage form to determine conformity with the target release property.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
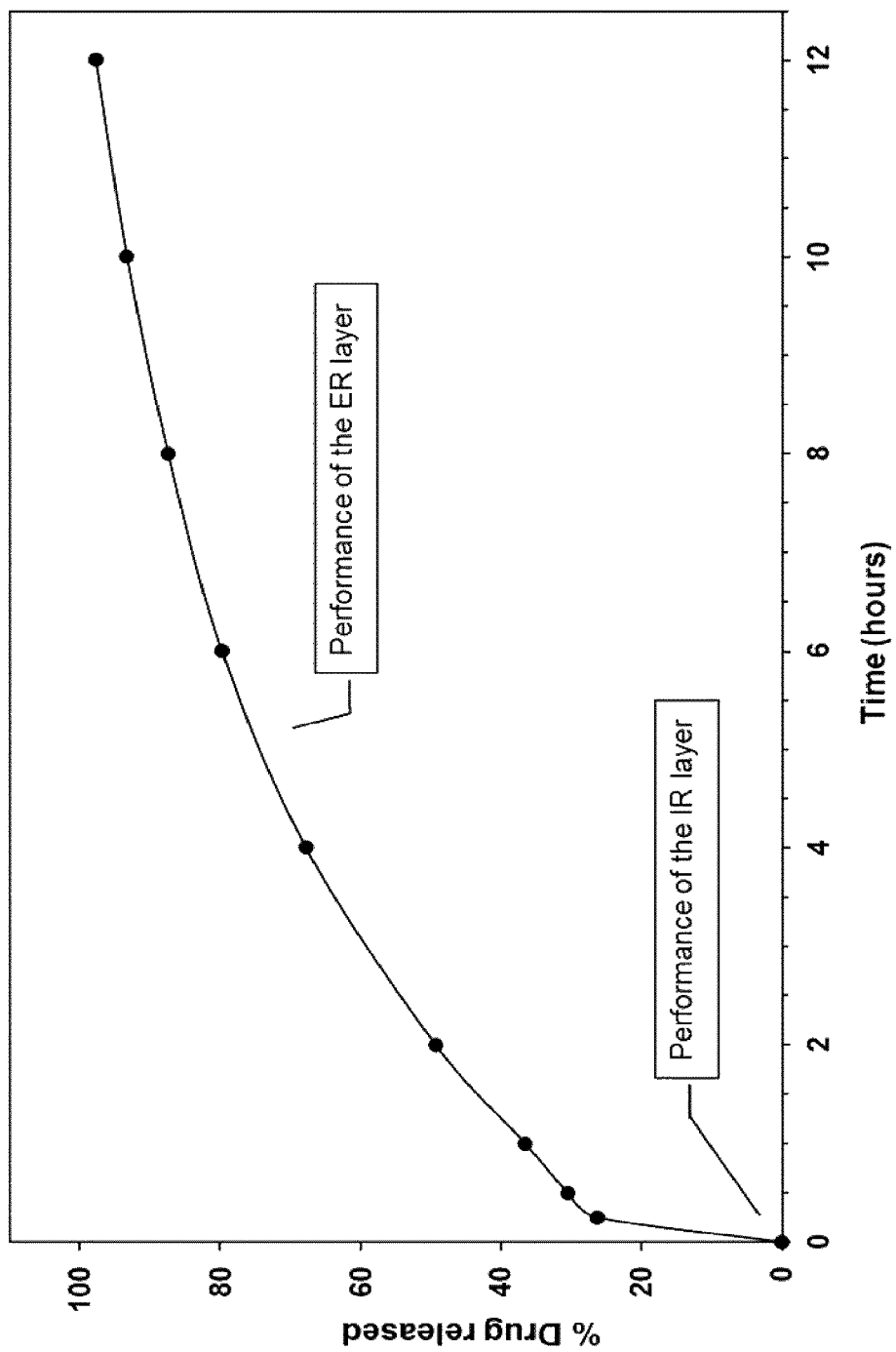
FIG. 1 depicts the proportion of API release in vitro over time shown as a measure of dissolution performance of intact acetaminophen dosage forms.

Generally, the present disclosure teaches extended release dosage forms comprising a release modifying excipient comprising blended high amylose starch, cross-linked hydroxypropylated amylopectin, and a pre-gelatinized common starch; wherein the released modifying excipient is substantially free of crosslinks between amylose and amylopectin and substantially free of crosslinks between amylose and amylose. Corresponding medical uses and methods are also provided; along with methods formulating a blend optimized for release of a particular active pharmaceutical agent.

It has been found that the release modifying properties of conventional CLHAS (e.g., Contramid®) can be reproduced in ER dosage forms by mixing; i) cross-linked chemically modified amylopectin; ii) a high amylose, non-chemically modified starch and; iii) a pre-gelatinized common starch according to some embodiments. This finding is surprising, as producing a release modifying excipient in this way means that no cross-linking of amylose to amylopectin occurs and no cross-linked amylose-amylose is present. These cross-linked components were previously considered vital for Contramid® function. The approach lends itself to flexible formulation processes in which the proportions of the blend components are adjusted to modify properties.

Dosage Forms

In one aspect, there is provided an extended release pharmaceutical dosage form comprising an active pharmaceutical ingredient (API) and a release modifying excipient, the release modifying excipient comprising 35 to 95% (wt/wt) of a high amylose starch, 1 to 40% (wt/wt) of a cross-linked hydroxypropylated amylopectin, and 1 to 30% (wt/wt) of a pre-gelatinized common starch, wherein the release modifying excipient is substantially free of cross-links between amylose and amylopectin subunits and substantially free of crosslinks between amylose and amylose subunits.

Where "wt/wt" amounts are specified in this context, this will be understood as being based on the total weight of the dosage form unless otherwise indicated.

By "active pharmaceutical ingredient (API)" is meant an agent that has a therapeutic or health-promoting effect when administered to a human or an animal, for example, an agent capable of treating or preventing a disease or condition. Examples of therapeutic agents include, but are not limited to, drugs, prodrugs, vitamins and supplements.

By "release modifying excipient" is meant an agent that, in a dosage form, affects the release rate of an API incorporated in the dosage form, such dosage form then releasing the API at a rate that is at least two-fold slower than would be achieved compared to an immediate release (IR) dosage form. CLHAS, hydroxypropyl cellulose (HPC), polyethylene oxide (PEO) sodium lauryl sulphate (SLS), copovidone, and hypromellose are release modifying excipients.

By "amylose" will be understood the component starch that is a helical polymer made from α-D-glucose units, bonded to each other through α(1→4) glycosidic bonds. Amylose is a linear carbohydrate, and is generally of lower molecular weight than amylopectin.

By "high amylose starch" (HAS) is meant a starch comprising of at least 50% amylose (wt/wt). Examples of commercially available HAS include Hylon VII™ Amylogel™ 03003, Hylon V, High Maize, Amylose Maize N400 and Eurylon G.

The high amylose starch may be non-chemically modified, i.e. free of chemical modification. For example, it may be non-crosslinked.

In one embodiment, the HAS comprises Hylon VII™.

By "amylopectin" will be understood the component starch is a polysaccharide and highly branched polymer of glucose. Glucose units are linked in a linear way with α(1→4) glycosidic bonds. Branching takes place with α(1→6) bonds occurring typically every 24 to 30 glucose units.

By "cross-linked hydroxypropylated amylopectin" (a type of cross-linked modified amylopectin, or "CMAP") is meant amylopectin that has been chemically modified to form covalent bonds between (and/or within) amylopectin molecules, and in which native amylopectin is substituted with hydroxypropyl groups. For example, hydroxypropylation may increase the gel stability, water solubility, digestibility, and storage stability of the native molecules. Examples include Utra-Tex4™, Pure-Gel B990™, Polar Tex-instant 12640™, and Polar-Tex-instant 12643™.

In one embodiment, the cross-linked hydroxypropylated amylopectin comprises Ultra-Tex4™.

By "pre-gelatinized common starch" (PGS) is meant a starch comprising not more than 50% amylopectin (wt/wt) that is subject to gelatinization, a process of breaking down the intermolecular bonds of starch molecules in the presence of water and heat, allowing the hydrogen bonding sites (the hydroxyl hydrogen and oxygen) to engage more water. Examples include Starch 1500™, SuperStarch 200™, and National 78-1551™.

In one embodiment, the PGS comprises Starch 1500™.

In one embodiment, the release modifying excipient comprises 35 to 95% (wt/wt) high amylose starch. In one embodiment, the release modifying excipient comprises 40 to 90% (wt/wt) high amylose starch. In one embodiment, the release modifying excipient comprises 45 to 85% (wt/wt) high amylose starch. In one embodiment, the release modifying excipient comprises 50 to 80% high amylose starch. In one embodiment, the release modifying excipient comprises 70 to 80% (wt/wt) high amylose starch.

In one embodiment, the release modifying excipient comprises 1 to 40% (wt/wt) of the cross-linked hydroxypropylated amylopectin. In one embodiment, the release modifying excipient comprises 5 to 30% (wt/wt) of the cross-linked hydroxypropylated amylopectin. In one embodiment, the release modifying excipient comprises 10 to 20% (wt/wt) of the cross-linked hydroxypropylated amylopectin.

In one embodiment, the release modifying excipient comprises 1 to 30% (wt/wt) of the pre-gelatinized common starch. In one embodiment, the release modifying excipient comprises 2 to 20% (wt/wt) of the pre-gelatinized common starch. In one embodiment, the release modifying excipient comprises 5 to 15% (wt/wt) of the pre-gelatinized common starch.

In one embodiment, the release modifying excipient comprises 55% to 65% (wt/wt) of the high amylose starch, 30% to 40% (wt/wt) of the cross-linked hydroxypropylated amylopectin, and 1% to 10% (wt/wt) of the pre-gelatinized common starch. In one embodiment, the release modifying agent comprises about 60% (wt/wt) of the high amylose starch, about 35% (wt/wt) of the cross-linked hydroxypropylated amylopectin, and about 5% (wt/wt) of the pre-gelatinized common starch. This is in accordance with Blend 1 (see Example 1).

By "about", as used herein, is meant within 10% above of or below the stated reference value.

In one embodiment, the release modifying excipient comprises 65% to 75% wt/wt) of the high amylose starch, 1% to 10% (wt/wt) of the cross-linked hydroxypropylated amylopectin, and 20% to 30% (wt/wt) of the pre-gelatinized common starch. In one embodiment, the release modifying agent comprises about 70% (wt/wt) of the high amylose starch, about 5% (wt/wt) of the cross-linked hydroxypropylated amylopectin, and about 25% (wt/wt) of the pre-gelatinized common starch. This is in accordance with Blend 2 (see Example 1).

In one embodiment, the release modifying excipient comprises 70% to 80% (wt/wt) of the high amylose starch, 10% to 20% (wt/wt) of the cross-linked hydroxypropylated amylopectin, and 5% to 15% (wt/wt) of the pre-gelatinized common starch. In one embodiment, the release modifying agent comprises about 75% (wt/wt) of the high amylose starch, about 15% (wt/wt) of the cross-linked hydroxypropylated amylopectin, and about 10% (wt/wt) of the pre-gelatinized common starch. This is in accordance with Blend 3 (see Example 1).

In one embodiment, the release modifying excipient comprises 85% to 95% (wt/wt) of the high amylose starch, 1% to 10% (wt/wt) of the cross-linked hydroxypropylated amylopectin, and 1% to 10% (wt/wt) of the pre-gelatinized common starch. In one embodiment, the release modifying agent comprises about 90% (wt/wt) of the high amylose starch, about 5% (wt/wt) of the cross-linked hydroxypropylated amylopectin, and about 5% (wt/wt) of the pre-gelatinized common starch. This is in accordance with Blend 4 (see Example 1).

In one embodiment, the API is an analgesic, anesthetic, serotonin reuptake inhibitor, 5-HT$_{2A}$ receptor antagonist, opiate receptor agonist, norepinephrine reuptake inhibitor, cardiovascular drug, metformin, or sulphonylurea.

By "analgesic" is meant any member of the group of drugs used to achieve reduction or relief of pain in mammals. Non-limiting examples include acetaminophen/paracetamol, nonsteroidal anti-inflammatory drugs (NSAIDs), COX-2 inhibitors, opioids, etc.

By "NSAID" is meant a non-narcotic drug that provides analgesic (pain-killing) and antipyretic (fever-reducing) effects, and, in higher doses, anti-inflammatory effects. Non-limiting examples include aspirin, ibuprofen, naproxen, flurbiprofen, and melxoicam.

By "COX-2 inhibitor" is meant a drug that selectively inhibits the cyclooxygenase-2 enzyme in mammals. In one embodiment, the COX-2 inhibitor comprises celecoxib By "anesthetic" is meant one of the drugs used to prevent pain in mammals, e.g. during surgery. Non-limiting examples of non-opioid anesthetics include Barbiturates (e.g. Amobarbital, Methohexital, Thiamylal, Thiopental), Benzodiazepines (e.g., Diazepam, Lorazepam, Midazolam), Etomidate, Ketamine, and Propofol.

Non-limiting examples of opioid anesthetics include Alfentanil, Fentanyl, Remifentanil, Sufentanil, Buprenorphine, Butorphanol, diacetyl morphine, Hydromorphone, Levorphanol, Meperidine, Methadone, Morphine, Nalbuphine, Oxycodone, Oxymorphone, Pentazocine, Tramadol, and Tapentadol.

By "serotonin reuptake inhibitor" is meant a drug that blocks the action of the serotonin transporter (SERT) in mammals and provides, for example, antidepressant, and antianxiety effects. Some examples include trazodone, tramadol, citalopram and vortioxetine.

By "5-HT$_{2A}$ receptor antagonist" is meant a drug that reduces the effects of the 5-HT2A receptor of mammals.

By "opiate receptor agonist" is meant a drug that enhances the effects of an opiate receptor of mammals.

By "norepinephrine reuptake inhibitor" is meant a drug that blocks the action of the norepinephrine transporter (NET) of mammals and provides, for example, psychostimulant effects, appetite suppressant effects, antidepressant, and antianxiety effects.

By "cardiovascular drug" is meant a drug that has an effect on the cardiovascular system of mammals.

In one embodiment, the API comprises acetaminophen.

In one embodiment, the API comprises celecoxib

In one embodiment, the API comprises flurbiprofen.

In one embodiment, the API comprises trazodone or a pharmaceutically acceptable salt thereof.

In one embodiment, the API comprises meloxicam or a pharmaceutically acceptable salt thereof.

In one embodiment, the API comprises metformin or a pharmaceutically acceptable salt thereof.

In one embodiment, the API comprises tramadol or a pharmaceutically acceptable salt thereof.

In one embodiment, the extended release pharmaceutical dosage form has substantially the same release profile and/or pharmacokinetics as a dosage form comprising an equivalent amount of cross-linked high amylose starch.

By "substantially the same" is meant less than a statistically significant difference between the release profile of the extended release pharmaceutical dosage form and the release profile of the reference pharmaceutical dosage form.

By "release profile" is meant the dissolution profile of the tablet and rate of release of the API.

In some embodiment, the extended release pharmaceutical dosage form exceeds the release profile and/or pharmacokinetics of a dosage form comprising an equivalent amount of cross-linked high amylose starch.

The term "exceeds" will be understood in context, such that when a low release rate is desirable, "exceeds" indicates an even lower release rate.

It has surprisingly been found that release modifying excipients, according to some embodiments, can recapitulate or exceed the release modifying properties of cross-linked high amylose starch. It is unexpected that a blend of ingredients, according to some embodiments, including pre-modified (e.g., cross-linked and hydroxypropylated) amylopectin, can recapitulate or exceed the release modifying properties of cross-linked high amylose starch, in which the components of the effective blend are modified together.

Release profiles can be compared using established statistical methods. For example, a difference factor ($f_1$) and a similarity factor ($f_2$) may be calculated for two curves using established methods.[3] In one embodiment, a release profile that is "substantially the same" may have an $f_1$ value from 0 to 15 and an $f_2$ value from 50 to 100. In one embodiment, the $f_1$ value may be up to 15. The $f_1$ value may be up to 10. The $f_1$ value may be up to 5. In one embodiment, a release profile that is "substantially the same" may have an $f_2$ value of 50 or greater. The $f_2$ value may be above 60. The $f_2$ value may 70 or greater. The $f_2$ value may be 80 or greater. The $f_2$ value may be 90 or greater.

In another embodiment, the extended release pharmaceutical dosage form has substantially the same release profile in dissolution media having pH 1 to 7.

In another embodiment, the extended release pharmaceutical dosage form has a lower release rate in an ethanol-containing dissolution media compared to non-ethanol-containing dissolution media. In some embodiments, the release rate in the ethanol-containing dissolution media may be substantially the same as that of a dosage form comprising an equivalent amount of cross-linked high amylose starch. In some embodiments, the release rate in the ethanol-containing dissolution media may be lower than that of a dosage form comprising an equivalent amount of cross-linked high amylose starch.

In another embodiment, the extended release pharmaceutical dosage has a drug loading level of at least 60%.

By "drug loading level" (DLL) as referred to herein is meant the weight ratio of the API to the total weight of the dosage form.

The DLL may be at least 5%. The DLL may be at least 10%. The DLL may be at least 15%. The DLL may be at least 20%. The DLL may be at least 25%. The DLL may be at least 30%. The DLL may be at least 35%. The DLL may be at least 40%. The DLL may be at least 45%. The DLL may be at least 50%. The DLL may be at least 55%. The DLL may be at least 60%. The DLL may be at least 65%. The DLL may be at least 70%. The DLL may be at least 75%. The DLL may be at least 80%. The DLL may be at least 85%. The DLL may be at least 90%.

In one embodiment, the extended release pharmaceutical dosage form is breakable. In one embodiment, the extended release pharmaceutical dosage form is scored.

In one embodiment, the extended release pharmaceutical dosage form is bisectable. In one embodiment, the extended release pharmaceutical dosage form is scored.

In one embodiment, the extended release pharmaceutical dosage form is tri-sectable. In one embodiment, the extended release pharmaceutical dosage form is scored.

In one embodiment, the extended release pharmaceutical dosage form is quarter-sectable. In one embodiment, the extended release pharmaceutical dosage form is scored.

By "scored" is meant notched, indented, or partially cut to facilitate subdivision. Any suitable modification to the dosage form that facilitates subdivision is intended.

In one embodiment, when the extended release pharmaceutical dosage form is subdivided, the subdivided portions have substantially the same release profile and/or pharmacokinetics as the intact dosage form. In one embodiment, the substantially the same release profile of the subdivided portions comprises an $f_2$ value of at least 50% with respect to the intact dosage form.

In one embodiment, upon subdivision, subdivided portions of the dosage form release less than 50% of the API at four hours, as measured in a USP Type III Apparatus in 900 mL of pH 6.8 phosphate buffer at 100 rpm at a temperature of 37° C.

In one embodiment, the extended release pharmaceutical dosage form comprises an IR portion comprising a first portion of the API, and a release modifying portion comprising a second portion of the API and the release modifying excipient.

By "immediate release" is meant that release of the API is not delayed upon ingestion, such that the biological effect is also note delayed beyond normal onset of action times.

In another aspect, the extended release pharmaceutical dosage form, the ratio of the release modifying excipient to the API in the release modifying portion is less than 1:7. The ratio may be between 1:1.5 to 1:7. In some embodiments it will be understood that these ratios are based on weights.

In one embodiment, the extended release pharmaceutical dosage provides an at least two-fold reduction in dosage frequency relative to an immediate release dosage form comprising the same amount of API.

In another aspect, the extended release pharmaceutical dosage form contains cross-linked hydroxypropylated amylopectin with no more than 7% (wt/wt) hydroxypropylated propyl groups.

In another aspect, the extended release pharmaceutical dosage form contains cross-linked hydroxypropylated amylopectin with no more than 0.04% (wt/wt) residual phosphate.

In another aspect, the extended release pharmaceutical dosage form contains cross-linked hydroxypropylated amylopectin with no more than 1 part per million of propylene chlorhydrin.

In another aspect, the extended release pharmaceutical dosage form comprises tramadol and a release modifying excipient, the release modifying excipient comprising 70-80% of the high amylose starch, 10-20% of the cross-linked hydroxypropylated amylopectin, and 5-15% of the pre-gelatinized common starch and the release modifying excipient is substantially free of crosslinks between amylose and amylopectin subunits and substantially free of crosslinks between amylose and amylose subunits. In one embodiment, the extended release pharmaceutical dosage form comprises 100 mg, 150 mg, 200 mg, or 300 mg of tramadol. In one embodiment, the extended release pharmaceutical dosage form is bisectable. In one embodiment, the extended release pharmaceutical dosage form is scored. In one embodiment, upon subdivision, the dosage form maintains substantially the same release profile for the tramadol as the intact dosage form. In one embodiment, the dosage form comprises 13 to 56% (wt/wt) tramadol and 5 to 20% (wt/wt) combined weight of the high amylose starch, the cross-linked hydroxypropylated amylopectin, and the pre-gelatinized common starch. In one embodiment, the dosage form comprises 22 to 33% (wt/wt) tramadol and 5 to 15% (wt/wt) combined weight of the high amylose starch, the cross-linked hydroxypropylated amylopectin, and the pre-gelatinized common starch. In one embodiment, upon subdivision, the two subdivided portions release less than 50% of the tramadol at four hours, as measured in a USP Type III Apparatus in 900 mL of pH 6.8 phosphate buffer at 100 rpm at a temperature of 37° C.

In another aspect, the extended release pharmaceutical dosage form comprises trazodone and a release modifying excipient, the release modifying excipient comprising 70-80% of the high amylose starch, 10-20% of the cross-linked hydroxypropylated amylopectin, and 5-15% of the pre-gelatinized common starch and the release modifying excipient is substantially free of crosslinks between amylose and amylopectin subunits and substantially free of crosslinks between amylose and amylose subunits. In one embodiment, the extended release pharmaceutical dosage form comprises 150 mg or 300 mg of trazodone. In one embodiment, the extended release pharmaceutical dosage form is bisectable. In one embodiment, the extended release pharmaceutical dosage form is scored. In one embodiment, upon subdivision, the dosage form maintains substantially the same release profile for the trazodone as the intact dosage form. In one embodiment, the dosage form comprises 25 to 75% (wt/wt) trazodone and 15 to 60% (wt/wt) combined weight of the high amylose starch, the cross-linked hydroxypropylated amylopectin, and the pre-gelatinized common starch. In one embodiment, the dosage form comprises 45 to 55% (wt/wt) trazodone and 27 to 38% (wt/wt) combined weight of the high amylose starch, the cross-linked hydroxypropylated amylopectin, and the pre-gelatinized common starch. In one embodiment, upon subdivision, the two subdivided portions release less than 50% of the trazodone at four hours, as measured in a USP Type III Apparatus in 900 mL of pH 6.8 phosphate buffer at 100 rpm at a temperature of 37° C.

In another aspect, the pharmaceutical dosage form comprises a bilayer with an immediate release portion comprising acetaminophen, and a release modifying portion comprising acetaminophen and a release modifying excipient comprising 70-80% of the high amylose starch, 10-20% of the cross-linked hydroxypropylated amylopectin, and 5-15% of the pre-gelatinized common starch, and the release modifying excipient is substantially free of crosslinks between amylose and amylopectin subunits and substantially free of crosslinks between amylose and amylose subunits. In one embodiment, the extended release pharmaceutical dosage form comprises 500 mg, 750 mg, or 1000 mg of acetaminophen. In one embodiment, the extended release pharmaceutical dosage form is bisectable. In one embodiment, the extended release pharmaceutical dosage form is scored. In one embodiment, upon subdivision, the dosage form maintains substantially the same release profile for the acetaminophen, as the intact dosage form. In one embodiment, the dosage form comprises 49 to 69% (wt/wt) acetaminophen and 3.5 to 13% (wt/wt) combined weight of the high amylose starch, the cross-linked hydroxypropylated amylopectin, and the pre-gelatinized common starch. In one embodiment, upon subdivision, the two subdivided portions release less than 50% of the acetaminophen at four hours, as measured in a USP Type III Apparatus in 900 mL of pH 6.8 phosphate buffer at 100 rpm at a temperature of 37° C.

In another aspect, the extended release pharmaceutical dosage form releases the API over at least 12 hours as measured using a USP Type III apparatus at a rate of 20 dips per minute, in a dissolution medium of 50 mM potassium phosphate buffer pH 6.8 (250 mL) at a temperature of 37° C.

The dosage form may release the API over at least 6, 8, 10, 12, or 14 hours.

In one embodiment, the extended release dosage form herein described further comprises an additional release modifying excipient. In one embodiment, the additional release modifying excipient may comprise hydroxypropyl methylcellulose ("hypromellose" or HPMC), hydroxypropyl methylcellulose blend, polyvinyl acetate/polyvinylpyrrolidone blend, and/or xanthan gum.

In one embodiment, the additional release modifying excipient comprises hydroxypropyl methylcellulose. The hydroxypropyl methylcellulose may be present in an amount of 1 to 50% w/w. In another embodiment, hydroxypropyl methylcellulose may be present in an amount of 5 to 35% w/w. In another embodiment, hydroxypropyl methylcellulose may be present in an amount of 10 to 20% w/w. In another embodiment, hydroxypropyl methylcellulose may be present in an amount of about 16% w/w.

In one embodiment, the hydroxypropyl methylcellulose may comprises, e.g., K100M. The K100M may be present in an amount of 1 to 50% w/w. In another embodiment, the K100M may be present in an amount of 5 to 35%. In another embodiment, the K100M may be present in an amount of 10 to 20% w/w. In another embodiment, the K100M may be present in an amount of about 16% w/w as in the Example 2 formulation.

In another embodiment, the hydroxypropyl methylcellulose may comprise a blend of K100 and K100M. The blend may be present in an amount of 1 to 90%. In another embodiment, the blend may be present in an amount of 2 to 30%. In another embodiment, the blend may be present in an amount of 3 to 15% w/w. In another embodiment, the blend may be present in an amount of about 5.4% w/w, as in the Example 1 formulation.

In another embodiment the additional release modifying excipient comprises a polyvinyl acetate/polyvinylpyrrolidone blend. The polyvinyl acetate/polyvinylpyrrolidone may be present in an amount of 10 to 90%. In another embodiment, the polyvinyl acetate/polyvinylpyrrolidone blend may be present in an amount of 30 to 70%. In another embodiment, the polyvinyl acetate/polyvinylpyrrolidone blend may be present in an amount of 45 to 55% w/w. In another embodiment, the polyvinyl acetate/polyvinylpyrrolidone blend may be present in an amount of about 40% w/w.

In another embodiment, the polyvinyl acetate/polyvinylpyrrolidone blend may comprise Kollidon SR. The Kollidon SR may be present in an amount of 10 to 90%. In another embodiment, the Kollidon SR may be present in an amount of 30 to 70%. In another embodiment, the Kollidon SR may be present in an amount of 45 to 55% w/w. In another embodiment, the Kollidon SR may be present in an amount of about 40% w/w, as in the formulation of Example 3.

In another embodiment the additional release modifying excipient comprises xanthan gum. The xanthan gum may be present in an amount of 10 to 90% w/w. In another embodiment, xanthan gum may be present in an amount of 30 to 70% w/w. In another embodiment, xanthan gum may be present in an amount of 15 to 25% w/w. In another embodiment, xanthan gum may be present in an amount of about 20% w/w.

In another embodiment, the xanthan gum may comprise Xantural 180. The Xantural 180 may be present in an amount of 10 to 90% w/w. In another embodiment, Xantural 180 may be present in an amount of 30 to 70% w/w. In another embodiment, Xantural 180 may be present in an amount of 15 to 25% w/w. In another embodiment, Xantural 180 may be present in an amount of about 20% w/w, as in the Example 3 formulation.

In one embodiment, the extended release dosage form further comprises a disintegrant. The disintegrant may be, for example, croscarmellose sodium, crospovidone, or sodium starch glycolate. For example, croscarmellose sodium (e.g. Vivasol) GF may be present in an amount of 0.05 to 5% w/w. In another embodiment, croscarmellose sodium may be present in an amount of 0.1 to 3% w/w. In another embodiment, croscarmellose sodium may be present in an amount of 0.25 to 1% w/w. In another embodiment, croscarmellose sodium may be present in an amount of about 0.45% w/w as in the Example 1 formulation.

In one embodiment, the extended release dosage form further comprises a glidant. In one embodiment, the glidant may be colloidal silicon dioxide or talc. For example, colloidal silicon dioxide (e.g. Cab-o-sil M-5P) may be present in an amount of 0.05 to 5% w/w. In another embodiment, colloidal silicon dioxide may be present in an amount of 0.1 to 3% w/w. In another embodiment, colloidal silicon dioxide may be present in an amount of 0.25 to 1% w/w. In another embodiment, colloidal silicon dioxide may be present in an amount of 0.39% w/w, 0.5% or 0.18%, respectively, as in the Examples 1, 2 and 3 formulations.

In one embodiment, the extended release dosage form further comprises a lubricant. In one embodiment, the lubricant may be hydrogenated vegetable oil, magnesium stearate or sodium stearyl fumarate. For example, magnesium stearate (e.g. Ligamed MF-2V) may be present in an amount of 0.05 to 5% w/w. In another embodiment, magnesium stearate may be present in an amount of 0.1 to 3% w/w. In another embodiment, magnesium stearate may be present in an amount of 0.25 to 1% w/w. In another embodiment, magnesium stearate may be present in an amount of about 0.5% as in the Example 3 formulation. In another embodiment, sodium stearyl fumarate (e.g. Pruv) may be present in an amount of 0.25 to 5%. In another embodiment, sodium stearyl fumarate I may be present in an amount of 0.5 to 3%. In another embodiment, sodium stearyl fumarate may be present in an amount of 1 to 2% w/w. In another embodiment, sodium stearyl fumarate may be present in an amount of 1.2% w/w and 1.5% w/w from examples 1 and 2 formulations. In another embodiment, hydrogenated vegetable oil e.g. Lubritab may be present in an amount of 0.05 to 10%. In another embodiment, hydrogenated vegetable oil may be present in an amount of 0.25 to 5%. In another embodiment, hydrogenated vegetable oil may be present in an amount of 0.5 to 1.5% w/w. In another embodiment, hydrogenated vegetable oil may be present in an amount of about 0.9% w/w as in the Example 3 formulation.

In one embodiment, the extended release dosage form further comprises a binder. In one embodiment, the binder may be carbomers, carboxymethyl cellulose, copovidone, hydroxypropyl cellulose, guar gum, polyethylene oxide or povidone. For example, copovidone may be present in an amount of 0.1 to 10% w/w. In another embodiment, copovidone may be present in an amount of 0.5 to 5% w/w. In another embodiment, copovidone may be present in an amount of 2 to 3% w/w. In another embodiment, copovidone may be present in an amount of about 2.3% w/w as in the Example 1 formulation.

Uses and Methods

In another aspect, there is provided a use of the extended release pharmaceutical dosage form describe herein for delivery of an API to a subject.

In another aspect, there provides a use of the extended release pharmaceutical dosage form describe herein for preparation of a medicament for delivery of an API to a subject.

In another aspect, there provides an extended release pharmaceutical dosage form as defined herein for use in delivery of an API to a subject.

In one aspect, there is provided a method of delivering an API to a subject comprising administering to the subject the pharmaceutical dosage form as described herein.

In one embodiment, the extended release pharmaceutical dosage form has substantially the same release profile and/or pharmacokinetics as a dosage form comprising an equivalent amount of cross-linked high amylose starch (e.g. Contramid).

The subject may be human.

The subject may be non-human. The subject may be a non-human mammal.

By "pharmaceutically effective level" is meant the minimum blood plasma concentration of API required to illicit the intended biological reaction or effect in a mammalian system.

The use, dosage form for use, or method may be for delivery the pharmaceutically effective level of the API for at least 8 hours, 10 hours, 12 hours or 24 hours.

In one embodiment, the use, dosage form for use, or method is for delivery of a pharmaceutically effective level of the API to the subject over at least 8 hours.

In one embodiment, the use, dosage form for use, or method is for delivery of a pharmaceutically effective level of the API to the subject over at least 10 hours.

In one embodiment, the use, dosage form for use, or method is for delivery of a pharmaceutically effective level of the API to the subject over at least 12 hours.

In another aspect, there is provided a use of a release modifying excipient comprising 35 to 95% (wt/wt) of a high amylose starch, 1 to 40% (wt/wt) of a cross-linked hydroxypropylated amylopectin, and 1 to 30% (wt/wt) of a pre-gelatinized common starch, wherein the release modifying excipient is substantially free of crosslinks between amylose and amylopectin subunits and substantially free of crosslinks between amylose and amylose subunits, for reproducing the release modifying property for an API of a CLHAS. Accordingly, the use would provide substantially the same release modifying property. In one embodiment, the use is for reproducing the release modifying property of an equivalent amount of a CLHAS. In one embodiment, the use is for exceeding the release modifying property of an equivalent amount of a CLHAS.

In another aspect, there is provided a release modifying excipient comprising 35 to 95% (wt/wt) of a high amylose starch, 1 to 40% (wt/wt) of a cross-linked hydroxypropylated amylopectin, and 1 to 30% (wt/wt) of a pre-gelatinized common starch, wherein the release modifying excipient is substantially free of crosslinks between amylose and amylopectin subunits and substantially free of crosslinks between amylose and amylose subunits, for use in reproducing the release modifying property for an API of a CLHAS. Accordingly, the release modifying excipient would provide substantially the same release modifying property. In one embodiment, the release modifying excipient is for use reproducing the release modifying property of an equivalent amount of a CLHAS. In one embodiment, the release modifying excipient is for use is for exceeding the release modifying property of an equivalent amount of a CLHAS.

Formulation Methods

In another aspect, there is provided a method for optimizing a release modifying excipient for an active pharmaceutical ingredient (API), the method comprising: selecting a target release property for a dosage from comprising the API, selecting an amount of a high amylose starch, selecting an amount of a cross-linked hydroxypropylated amylopectin, and selecting an amount of a pre-gelatinized common starch, blending the high amylose starch, the cross-linked hydroxypropylated amylopectin, and the pre-gelatinized common starch using the selected amounts to form a release modifying excipient, wherein the release modifying excipient is substantially free of crosslinks between amylose and amylopectin subunits and substantially free of crosslinks between amylose and amylose subunits, forming a dosage form comprising the API and the release modifying excipient, and testing the dosage form to determine conformity with the target release property.

In some embodiments, the flexibility afforded by the ability to blend pre-existing ingredients means that the release modifying properties of the release modifying excipient can be more readily adjusted or tailored to an API of interest, and/or to recapitulate or exceed the release modifying properties of a dosage form comprising another release modifying excipient, such as a conventional CLHAS. In some embodiments, an aim is to recapitulate the release modifying properties of a dosage form comprising another release modifying excipient, such as a conventional CLHAS.

By "target release property" is meant, in some embodiments, the desired API dissolution rate from the dosage form.

In one embodiment, the target release property is from a reference dosage form. In one embodiment, the target release property is from a reference dosage form comprising the API and a conventional cross-linked high amylose starch release modifying excipient.

In one embodiment, the amount of release modifying excipient in the dosage form does not exceed the amount of cross-linked high amylose starch release modifying excipient in the reference dosage form.

In one aspect, there is provided a method of mixing the amylose starch, the cross-linked hydroxypropylated amylopectin, and the pre-gelatinized common starch described herein to form the release modifying excipient described herein.

In one aspect, there is provided a method of mixing the release modifying excipient defined herein with the API to form the dosage form described herein.

In one embodiment, the release modifying excipient may comprise any one or more of the properties herein described.

For example, the release modifying excipient may comprises 35 to 95% (wt/wt) of a high amylose starch, 1 to 40% (wt/wt) of a cross-linked hydroxypropylated amylopectin, and 1 to 30% (wt/wt) of a pre-gelatinized common starch.

In one embodiment, the release modifying excipient comprises 35 to 95% (wt/wt) high amylose starch. In one embodiment, the release modifying excipient comprises 40 to 90% (wt/wt) high amylose starch. In one embodiment, the release modifying excipient comprises 45 to 85% (wt/wt) high amylose starch. In one embodiment, the release modifying excipient comprises 50 to 80% high amylose starch. In one embodiment, the release modifying excipient comprises 70 to 80% (wt/wt) high amylose starch.

In one embodiment, the release modifying excipient comprises 1 to 40% (wt/wt) of the cross-linked hydroxypropylated amylopectin. In one embodiment, the release modifying excipient comprises 5 to 30% (wt/wt) of the cross-linked hydroxypropylated amylopectin. In one embodiment, the release modifying excipient comprises 10 to 20% (wt/wt) of the cross-linked hydroxypropylated amylopectin.

In one embodiment, the release modifying excipient comprises 1 to 30% (wt/wt) of the pre-gelatinized common starch. In one embodiment, the release modifying excipient comprises 2 to 20% (wt/wt) of the pre-gelatinized common starch. In one embodiment, the release modifying excipient comprises 5 to 15% (wt/wt) of the pre-gelatinized common starch.

In one embodiment, the release modifying excipient comprises 55% to 65% (wt/wt) of the high amylose starch, 30% to 40% (wt/wt) of the cross-linked hydroxypropylated amylopectin, and 1% to 10% (wt/wt) of the pre-gelatinized common starch. In one embodiment, the release modifying agent comprises about 60% (wt/wt) of the high amylose starch, about 35% (wt/wt) of the cross-linked hydroxypropylated amylopectin, and about 5% (wt/wt) of the pre-gelatinized common starch. This is in accordance with Blend 1 (see Example 1).

In one embodiment, the release modifying excipient comprises 65% to 75% wt/wt) of the high amylose starch, 1% to 10% (wt/wt) of the cross-linked hydroxypropylated amylopectin, and 20% to 30% (wt/wt) of the pre-gelatinized common starch. In one embodiment, the release modifying agent comprises about 70% (wt/wt) of the high amylose starch, about 5% (wt/wt) of the cross-linked hydroxypropylated amylopectin, and about 25% (wt/wt) of the pre-gelatinized common starch. This is in accordance with Blend 2 (see Example 1).

In one embodiment, the release modifying excipient comprises 70% to 80% (wt/wt) of the high amylose starch, 10% to 20% (wt/wt) of the cross-linked hydroxypropylated amylopectin, and 5% to 15% (wt/wt) of the pre-gelatinized common starch. In one embodiment, the release modifying agent comprises about 75% (wt/wt) of the high amylose starch, about 15% (wt/wt) of the cross-linked hydroxypropylated amylopectin, and about 10% (wt/wt) of the pre-gelatinized common starch. This is in accordance with Blend 3 (see Example 1).

In one embodiment, the release modifying excipient comprises 85% to 95% (wt/wt)of the high amylose starch, 1% to 10% (wt/wt)of the cross-linked hydroxypropylated amylopectin, and 1% to 10% (wt/wt) of the pre-gelatinized common starch. In one embodiment, the release modifying agent comprises about 90% (wt/wt) of the high amylose starch, about 5% (wt/wt) of the cross-linked hydroxypropylated amylopectin, and about 5% (wt/wt) of the pre-gelatinized common starch. This is in accordance with Blend 4 (see Example 1).

EXAMPLES

Introduction

Starch-based excipients can be used for formulation of drugs, e.g. with the intention of making such drugs long-acting or to have prolonged effectiveness. Such excipients have the ability to control the dissolution of the API in the gastrointestinal environment e.g. to allow it to take place continuously over a period of at least 8 hours as benefits certain drug types e.g. analgesics or CNS drugs.

The gelling properties of a starch-based excipient are dependent on the ratio between two essential sub-components, namely amylopectin and amylose. To be useful as an excipient in ER tablets, a formulation must balance the ratio of amylopectin and amylose content to achieve a gel with an effective viscosity as well as achieve an effective gelling speed. The state of the art shows that starting material corn starches containing 50% amylose content or more (high amylose starches [HAS]) are more useful in producing ER tablets than those with less than 50% amylose content.

With the above-noted shortcomings of CLHAS, tests were designed and conducted to determine whether blends of various starch ingredients could match or exceed the performance of commercially available conventional CLHAS used in commercially available pharmaceutical formulations.

Example 1: Acetaminophen Dosage Form

Dosage Form Manufacture

A summary of the starch blends prepared (Test Blends) is found in Table 1.

TABLE 1

| Raw Material | Test Blend 1 | Test Blend 2 | Test Blend 3 | Test Blend 4 |
|---|---|---|---|---|
| HAS | 60 | 69.5 | 75 | 90 |
| CMAP | 35 | 5 | 15 | 5 |
| PGS | 5 | 25.5 | 10 | 5 |

CMAP indicates a cross-linked modified amylopectin, in this case a cross-linked hydroxypropylated amylopectin. In these experiments, Ultra-Tex 4™ was used.

HAS indicates a high amylose starch. In these experiments, Hylon VII™ was used.

PG indicates a pre-gelatinized common starch. In this case, Starch 1500™ was used.

Acetaminophen was used as an API to evaluate the release modifying properties of the Test Blends in Table 1. Acetaminophen was selected as an API to provide a meaningful comparison between tablets made using each of the Test Blends and identical tablets manufactured with a commercially available conventional CLHAS (Contramid®), known to be part of a clinically validated bilayer tablet.

The Test Blend containing tablets, comprised an immediate release (IR) layer designed to achieve an early rapid release of acetaminophen and thereby an early onset of analgesia, and an extended release (ER) layer comprising one of the Test Blends designed to extend analgesia for up to 12 hrs.

Control tablets, comprising an equal amount of Contramid® were also manufactured. The quantitative composition of the acetaminophen formulations is provided in Table 2 where the components of each layer are indicated.

TABLE 2

| Raw material | mg/tab | % w/w |
|---|---|---|
| IR Layer Components | | |
| Acetaminophen 90% (as Compap*) | 166.7 | 14.25 |
| Microcrystalline Cellulose PH102 | 84.8 | 7.24 |
| Colloidal Silicon Dioxide | 1.3 | 0.11 |
| Sodium Stearyl Fumerate | 3.9 | 0.34 |
| FD&C Aluminum Lake Blue N° 1 (13%) | 0.1 | 0.01 |
| Croscarmellose Sodium | 5.2 | 0.45 |

TABLE 2-continued

| Raw material | mg/tab | % w/w |
|---|---|---|
| CR Layer Components | | |
| Acetaminophen 90% (as Compap*) | 666.7 | 56.98 |
| Microcrystalline Cellulose PH102 | 41.6 | 3.55 |
| HPMC K100 Premium-LVCR | 38.1 | 3.26 |
| HPMC K100M Premium-CR | 25.4 | 2.17 |
| Copovidone | 27.2 | 2.33 |
| Colloidal Silicon Dioxide | 4.5 | 0.39 |
| Sodium Stearyl Fumerate | 13.6 | 1.16 |
| Contramid ® or Novel Test Blend | 90.8 | 7.76 |
| Total: | 1170.0 | 100.0 |

It is noted that Compap is a compressible form of acetaminophen comprising 90% acetaminophen along with other directly compressible excipients. Total acetaminophen content was 750 mg.

Tablets were manufactured by blending the raw material components of the IR and ER layers separately using a V blender. Separate ER blends were made for each of the starch blends shown in Table 1 and for the control, Contramid containing blend. Each of the ER blends was then compressed with IR blend using a bilayer tablet press to achieve the final compressed tablet. The press tooling used for manufacture of the tablets included a score to allow easy breaking of the tablets. The compressed tablets were then coated with a non-functional aesthetic film prior to dissolution testing in both intact and bisected form.

Testing

The tablets were assessed for their dissolution performance in both intact and bisected forms. The dissolution method employed USP Type III apparatus at a rate of 20 dips per minute. The dissolution medium used was 50 mM potassium phosphate buffer pH 6.8 (250 mL) at a temperature of 37° C.±0.5° C. Dissolution tests were conducted on 6 tablets sampling at various interval times over a 12-hour period to establish a full dissolution profile. The acetaminophen concentrations in the various samples were assessed using RP-HPLC and UV detection.

The pharmacokinetic performance of the control tablets was assessed in humans as part of a study to assess the safety and efficacy of the tablets. Briefly, 48 subjects undergoing impacted third molar extraction were administered 2 tablets immediately after surgery. Three millilitre blood samples were collected by indwelling catheters before the dose (time 0), and at 0.5, 1, 1.5, 2, 2.5, 3, 3.5, 4, 5, 6, 7, 8, 10, and 12 hours after the dose. The acetaminophen concentration in each sample was then determined by specific bioassay. The following single-dose pharmacokinetic parameters for acetaminophen in plasma were then estimated using non-compartmental methods: area under the plasma concentration-time curve to the last quantifiable concentration (AUC); area under the plasma concentration-time curve extrapolated to infinity (AUCINF); percentage of AUCINF obtained by extrapolation (% AUC, exp); maximum plasma concentration (CMAX); maximum time (TMAX); apparent terminal rate constant and half-life (T½).

Results

FIG. 1 shows in vitro dissolution performance of the control tablets which serves as a benchmark for subsequent in vitro tests.

Figure 2:
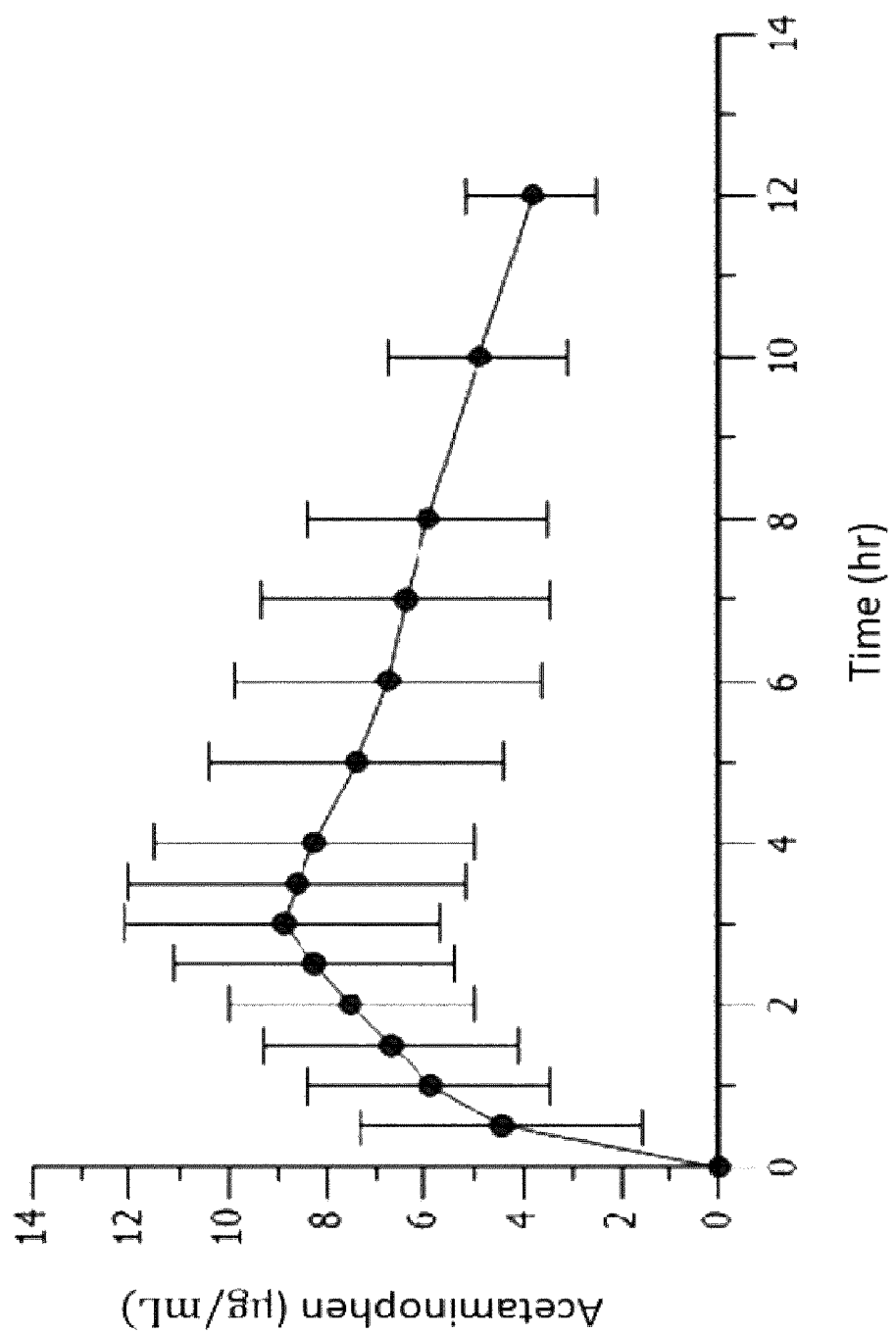
FIG. 2 depicts mean plasma acetaminophen concentrations over time as generated by dosage forms of composition according to Table 2. The biphasic nature of the in vitro dissolution profile is reflected in the in vivo pharmacokinetics generated by the dosage forms.

FIG. 2 shows the mean plasma acetaminophen concentrations over time as generated by the control tablets. The biphasic nature of the in vitro dissolution profile is reflected in the in vivo pharmacokinetics generated by the tablets. The pharmacokinetic parameters calculated are shown in Table 3.

TABLE 3

| Parameter | Value |
|---|---|
| Mean exposure (AUC) | 74.433 µg · h/mL |
| Mean (AUC$_{INF}$) | 100.46 µg · h/mL |
| Mean max plasma concentration (C$_{max}$) | 9.889 µg/mL |
| Absorption rate (T$_{max}$) | 3.331 hrs |
| Mean apparent terminal rate constant | 0.144 l/h |
| Mean half-life (T$_{1/2}$) | 5.381 hrs |

Figure 3:
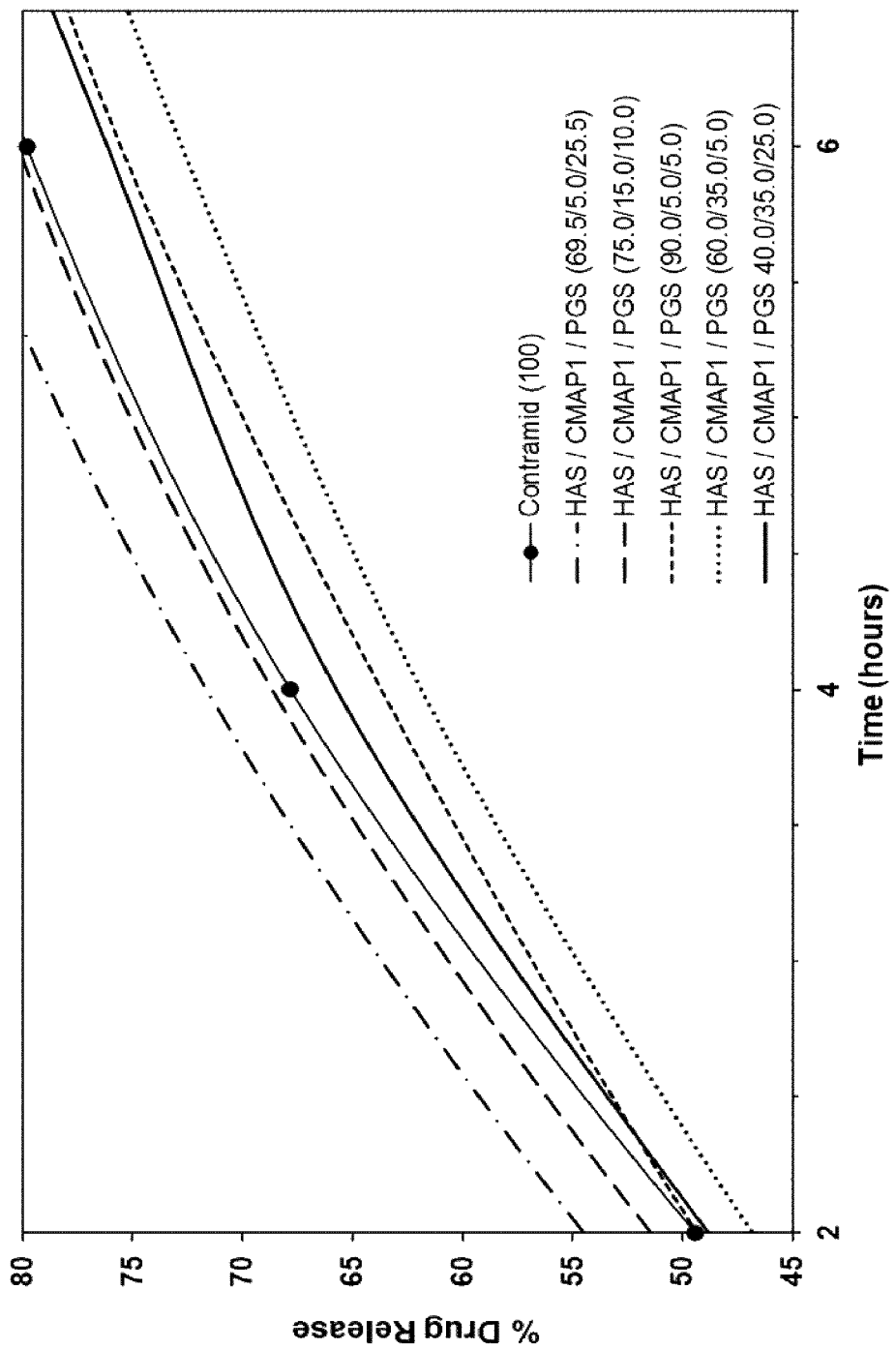
FIG. 3 depicts the proportion of acetaminophen released over time from acetaminophen dosage forms manufactured with ER layers comprising each of the starch Test Blends shown in Table 1. Test Blends generating faster, identical and slower release of acetaminophen over time compared to Contramid were identified.

FIG. 3 shows the dissolution performance of tablets with ER layers comprising one each of the Test Blends shown in Table 1.

These results show that, contrary to previous teachings, simple mixtures of the three starches constituting each of the blends in Table 1 maintained the extended release characteristics of the ER layer. Cross-linking of amylose to amylose, amylose to amylopectin and amylopectin was not needed.

Further, blending the starch components shown in the different proportions shown in Table 1 resulted in blends with different release modifying properties with some generating ER layers that released acetaminophen more slowly than was achieved by the control and some that released acetaminophen more rapidly. Simple mixing is therefore able to generate a more versatile release modifying excipient than Contramid, which as a conventional CLHAS has a fixed proportion of amylose to amylopectin and where amylose-amylose, amylose-amylopectin and amylopectin-amylopectin cross links exist.

Contrary to previous teachings simple blends of the three starches constituting each of the blends in Table 1 have been shown to maintain the extended release characteristics of the ER layer. Cross-linking of amylose to amylose, and of amylose to amylopectin, was not needed.

Blending the three starches in different proportions resulted in different extended release properties some generating ER layers that released acetaminophen more slowly than was achieved by Contramid® and some that released acetaminophen more rapidly. Simple mixing is therefore able to generate a more versatile excipient than Contramid®.

Test Blend 3 generated an f2 similarity factor above 50 (see FIG. 3). An f2 factor above 50 indicates that the tablets, manufactured using the novel triple blend will be bio-equivalent in vivo to those manufactured with Contramid® i.e. that they will generate the data bio-equivalent to those shown in FIG. 2 and Table 3.

Figure 4:
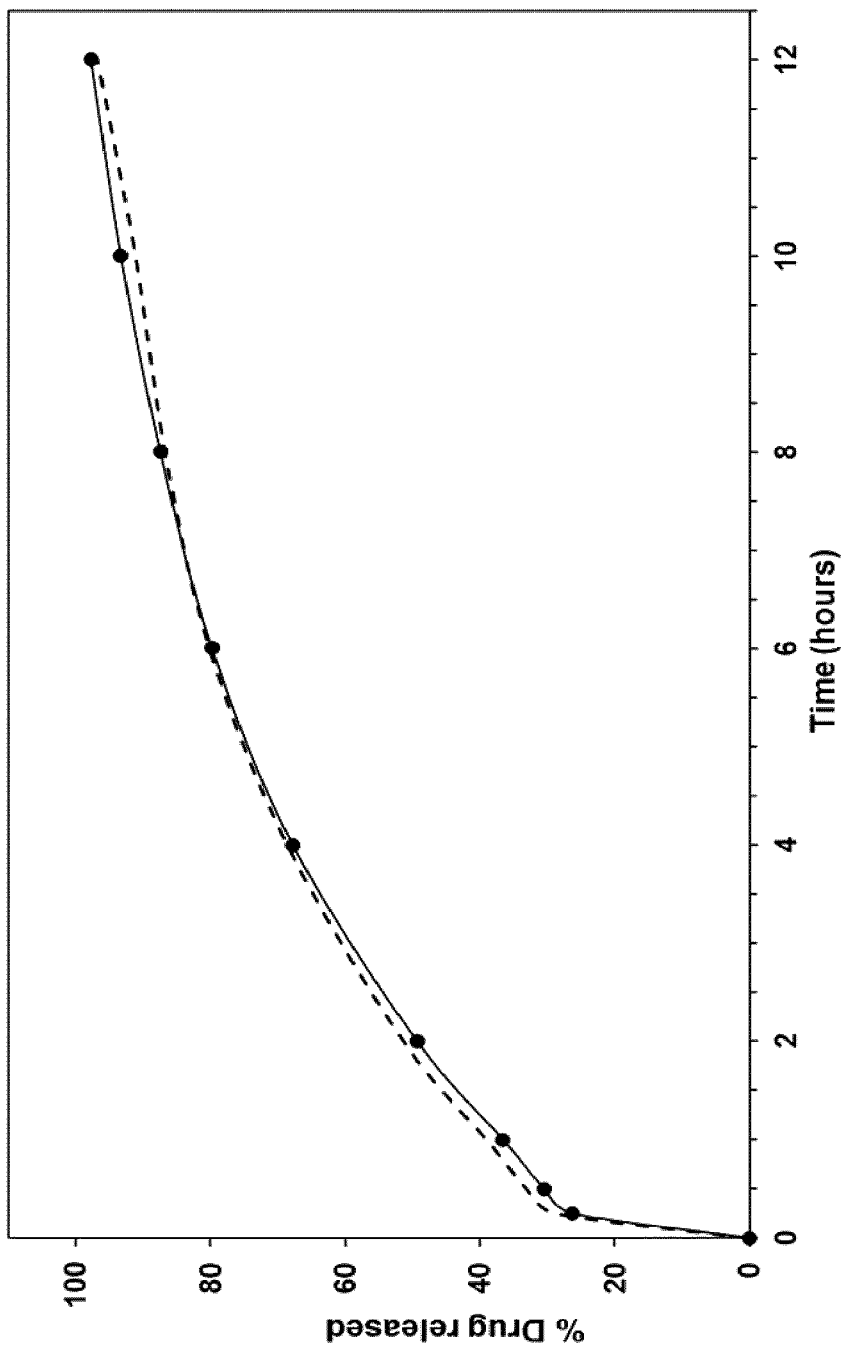
FIG. 4 depicts the proportion of API released as a measure of dissolution performance of the bilayer acetaminophen formulation with ER layer comprising Contramid® or the HAS/CMAP/PGS blend.

FIG. 4 demonstrates in vitro dissolution performance of acetaminophen tablets comprising equal amounts of either Contramid or Test Blend 3 in their ER layers. The same degree of extended release was achieved whether Test Blend 3 or Contramid was used. The Test Blend 3 composition of HAS:CMAP:PGS of 75:15:10 thus generated an ER layer which best matched the performance of the ER layer comprising Contramid®.

A conventional CLHAS, such as Contramid®, has the ability to retain the extended release characteristics of an ER tablet despite the tablet being broken. This feature is valuable since it protects patients from the uncontrolled, sudden release of drug (dose dumping) that will occur when tablets comprising conventional ER tablet technologies are broken and the subsequent potentially dangerous increases in API concentration in the blood that occur as a consequence. It is important therefore that any replacement for a conventional CLHAS such as Contramid® retains this feature.

Figure 5:
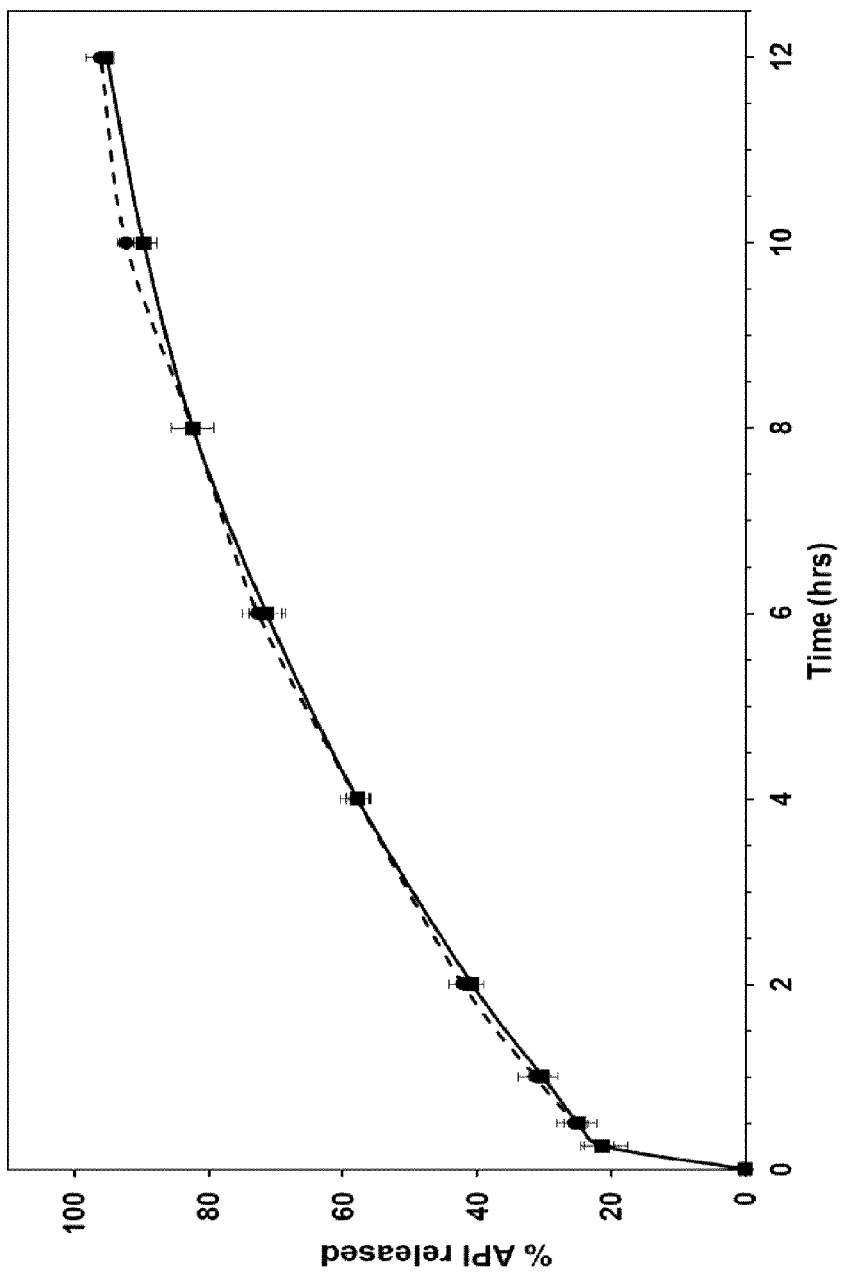
FIG. 5 depicts the proportion of API released as a measure of dissolution performance of the acetaminophen dosage forms shown in FIG. 4 in both the intact and bisected form.

The dissolution performance of the tablets shown in FIG. 4 in both the intact and bisected form, was therefore assessed using the dissolution method described above. FIG. 5 depicts these results. As is evident, intact and bisected tablets comprising Test Blend 3 displayed the same dissolution profiles with an f2 of 90. The release rate of acetaminophen was unchanged by breaking the tablet. Results for the half tablets were dose normalized. No dose dumping occurs.

Example 2: Trazodone 24-hour Dosage Form

The performance of the 75:15:10 blend was validated by using it to replace Contramid® in an existing Contramid® ER tablet (Contramid® Trazodone 24 hr ER tablets as described in U.S. Pat. No. 8,414,919). These tablets were single layer scored tablets made by blending and then compression of the raw materials shown in Table 4.

TABLE 4

| Raw material | mg/tab | % w/w |
|---|---|---|
| Trazodone HCl | 300.0 | 49.0 |
| HPMC K100M | 100.0 | 16.3 |
| Silicon dioxide | 3.0 | 0.5 |
| Sodium stearyl fumerate | 9.0 | 1.5 |
| Contramid ® or Starch Blend 75:15:10 | 200 | 32.7 |
| Total: | 612.0 | 100.0 |

Here, the "Starch Blend 75:15:10" corresponds to Blend 3 described in Table 1. The dissolution performance of the both tablet formulations was assessed using USP Type II (Paddle) apparatus operating at a rate of 50 rpm. The dissolution medium used was water (900 mL) at a temperature of 37° C.±0.5° C. Dissolution tests were conducted on 6 tablets sampling at various interval times over a 24 hr period to establish a full dissolution profile. The trazodone concentrations in the various samples were assessed using RP-HPLC and UV detection.

Figure 6:
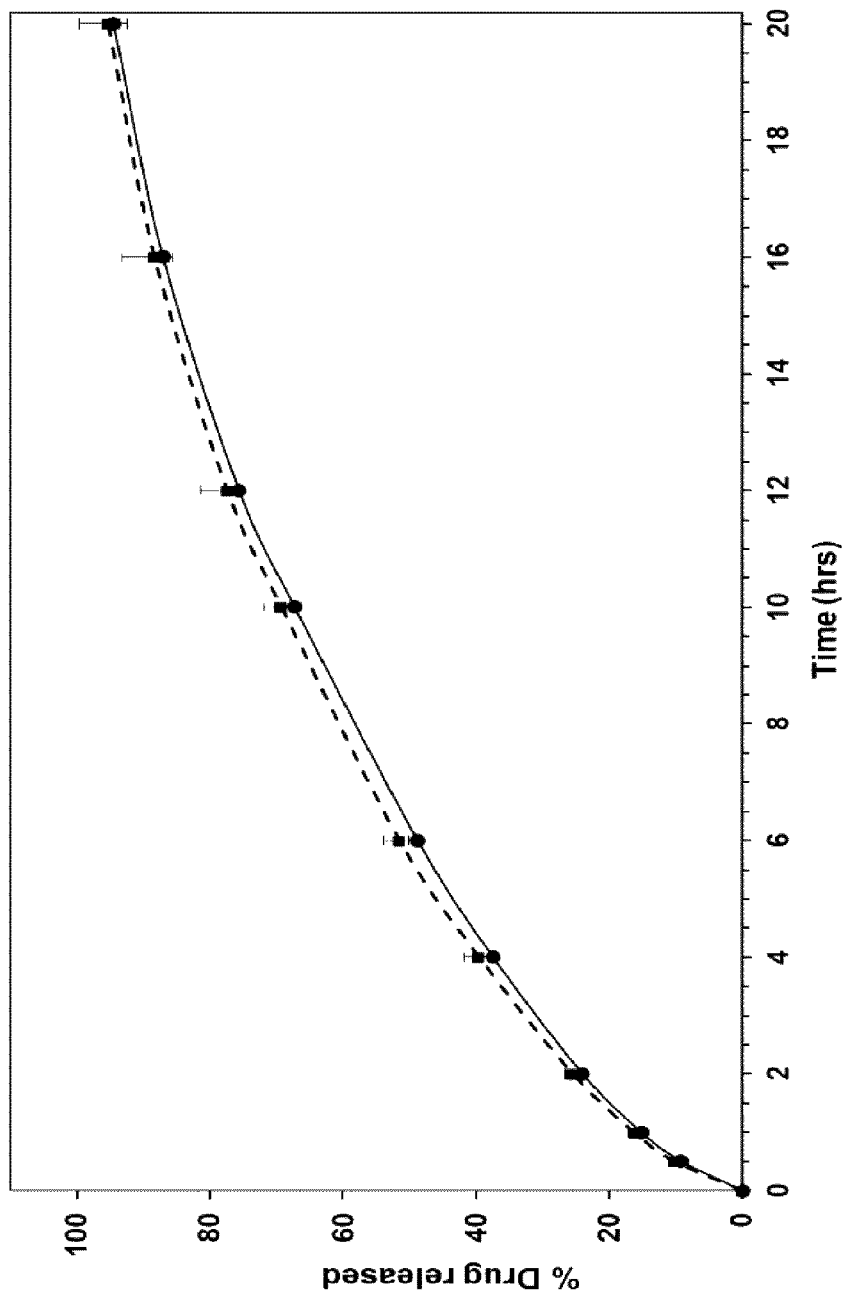
FIG. 6 depicts the proportion of API released as a measure of comparative in vitro dissolution performance of trazodone ER dosage forms manufactured using Contramid® or the 75:15:10 starch blend.

FIG. 6 depicts in vitro release of trazodone from dosage forms comprising and equal amount of either Test Blend 3 or Contramid®. Tablets made with either Contramid® or Test Blend 3 displayed the same in vitro dissolution performance, the latter generating an f2 value of 80 versus the Contramid® version. The starch blend was therefore able to replace Contramid® in this tablet formulation.

Example 3: Tramadol 24-Hour Dosage Form

The performance of the 75:15:10 blend was further validated by again using it to replace Contramid® in a novel ER tramadol hydrochloride tablet designed to display 24 hr dissolution performance. These tablets were single layer scored tablets made by blending and then compression of the raw materials shown in Table 5.

TABLE 5

| Raw material | mg/tab | % w/w |
|---|---|---|
| TRAMADOL HCL | 300.00 | 27.264% |
| Starch Blend 75:15:10 (Blend 3) | 118.55 | 10.774% |
| Kollidon SR | 443.39 | 40.296% |
| Xanthan gum 80 mesh | 221.71 | 20.149% |
| Hydrogenated vegetable oil | 9.82 | 0.892% |
| Colloidal Silicon Dioxide | 1.96 | 0.178% |
| Magnesium stearate | 4.91 | 0.446% |
| Total: | 1100.34 | 100% |

The dissolution performance of these tablets was tested replacing the pH 6.8 dissolution medium with the following:
pH 1.2 dilute hydrochloric acid,
pH 4.5 50 mM phosphate buffer,
40% ethanol in pH 6.8, phosphate buffer.

Figure 7:
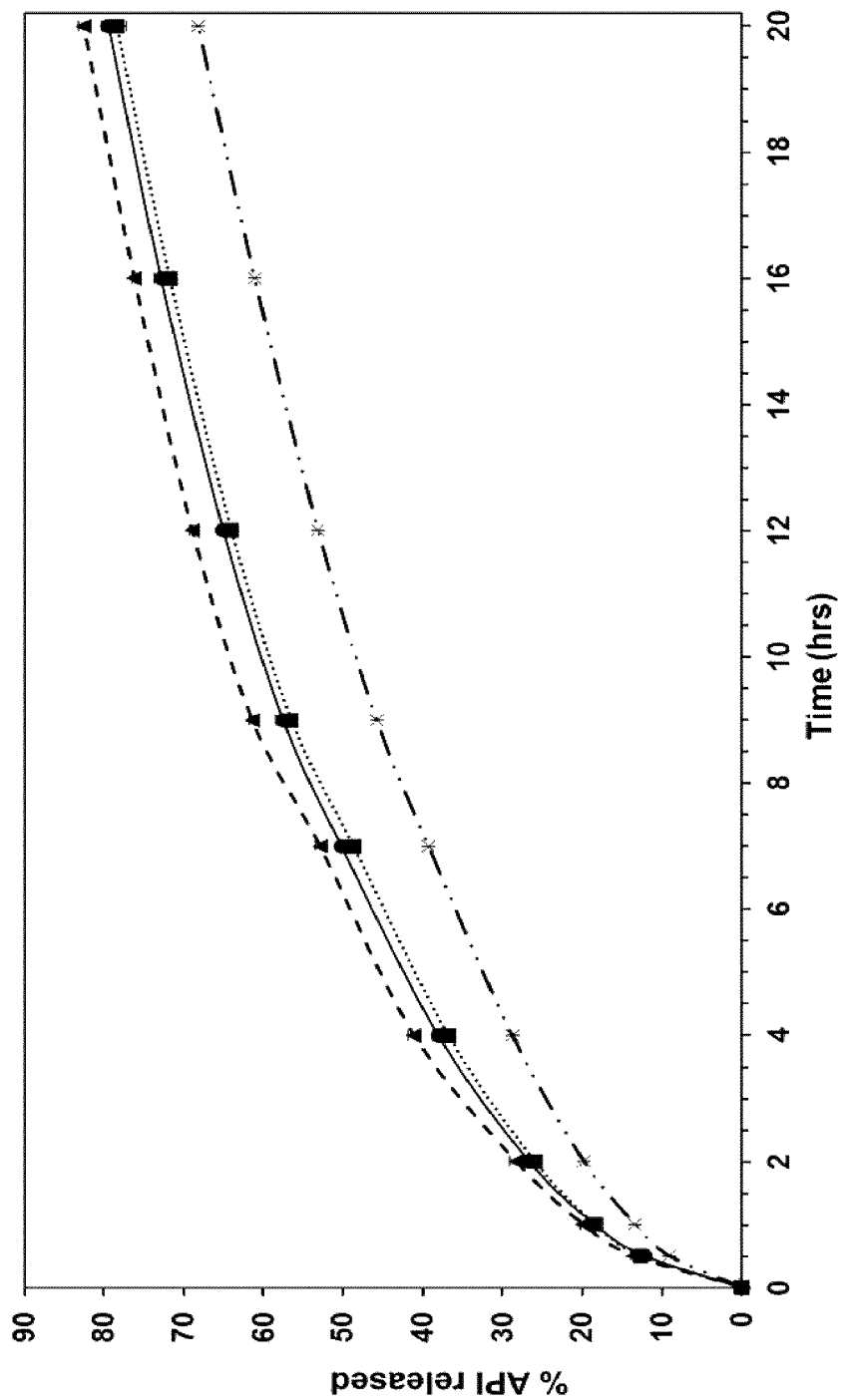
FIG. 7 depicts dissolution profiles for tramadol formulations across a pH range, and in alcohol. Large circles (on the black line) indicate pH 6.8, black squares (on the black small dotted line) indicate pH 4.5, black triangles (on the black large dotted line) indicate pH 1.2, and black asterisks (on the bottom-most line) indicate 40% ethanol at pH 6.8.

FIG. 7 shows the dissolution rate in pH 1.2, pH 4.5, pH 6.8 and in 40% ethanol (*) (the latter condition selected to mimic administration with alcoholic beverages). Evident is that the novel starch containing tablets provide dissolution rate for API that are independent of pH from pH 1.2 to pH 6.8, conditions relevant to those found in the gastrointestinal tract of humans. Also evident is that, unlike film based ER tablet technologies which dose dump under these conditions, the release rate of the tablets in 40% ethanol is lower than that in purely aqueous media. This is feature protects patients from the harmful effects of dose dumping but also reduces the impact of enhanced drug absorption that can occur when API such as tramadol are administered with alcohol.

A further tramadol dosage form was made by blending and compressing the raw materials show in Table 6.

TABLE 6

| Raw material | mg/tab | % w/w |
|---|---|---|
| TRAMADOL HCL | 300.00 | 27.518% |
| Starch Blend 75:15:10 (Blend 3) | 118.55 | 10.874% |
| Xanthan gum 80 mesh | 664.76 | 60.977% |
| Colloidal Silicon Dioxide | 1.96 | 0.180% |
| Magnesium stearate | 4.91 | 0.450% |
| Total: | 1090.19 | 100% |

The dosage form was also scored for subdivision into halves.

Figure 8:
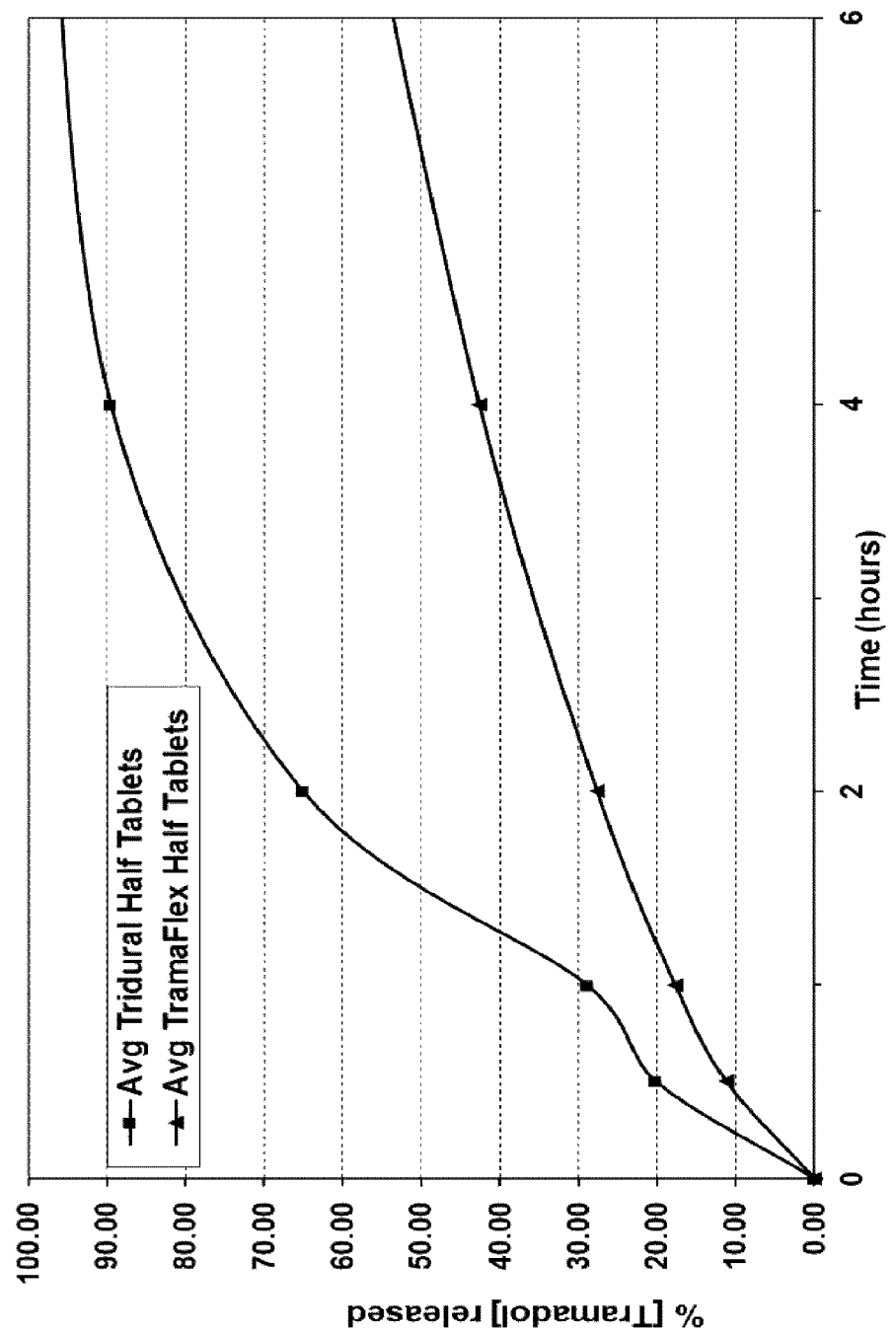
FIG. 8 shows dissolution profiles for subdivided halves of a tramadol formulation comprising the novel release modifying excipient (bottom curve) versus a comparable tramadol formulation (Tridural®) comprising Contramid.

FIG. 8 shows in vitro dissolution profiles of the subdivided halves of this formulation (bottom curve) as versus a comparable controlled release tramadol formulation (Tridural®) comprising Contramid. Profiles were measured in a Type I USP Dissolution Apparatus in 900 mL pH 6.8 phosphate buffer at 100 rpm. Dose dumping for the latter is evident, with Tridural® displaying a significantly accelerated rate of release, and releasing almost 90% of it tramadol by four hours, as compared to about 40% release of tramadol for the above-described formulation (Table 6) comprising the novel release-modifying excipient (Test Blend 3). Test Blend 3 containing tablets displayed a release rate that is substantially the same, whether intact or broken. In this sense the novel excipient outperforms Contramid®.

Discussion of Examples

Extended release dosage forms are valuable to the patient due to their convenience and because they promote compliance.

Previously scientific literature taught that only cross linked high amylose starches comprising cross linked chemically modified amylose-amylose molecules, cross-linked chemically modified amylose-amylopectin molecules, and cross linked chemically modified amylopectin-amylopectin molecules, could be used in the manufacture of extended release dosage forms. Contrary to this, it has been shown herein that a blend of cross linked and chemically modified amylopectin, physically and intimately mixed with a non-cross linked high amylose starch and a pregelatinized starch can effectively reproduce the performance of a conventional CLHAS (Contramid®) when included in extended release tablets tested both in vitro and in vivo. Further, it has been confirmed that the safer use features imparted by conventional CLHAS (as described in U.S. Pat. No. 8,414,919)—e.g., allowing extended release dosage forms to be broken without dose dumping, and the avoidance of dose-dumping in the presence of alcohol—can also be maintained by such a blend.

Previously, it was believed that conventional CLHAS would allow tablet breaking. Here, it has been shown, while this is the case for the novel blend, it is not the case for the conventional CLHAS, Contramid. The new blend outperformed Tridural®, a Contramid®-containing tramadol formulation for dose dumping.

In addition it has been demonstrated that by varying the ratio of the three starches included in the blend, the extended release properties of the novel starch drug release modifying excipient can be changed, thereby allowing greater versatility in modifying release delivery of a wider range of APIs. The fact that the materials used to prepare the blend can be purchased from a number of suppliers, decreases the likelihood of supply issues, while ensuring price competition and a reduction in cost of goods that may be passed on to the patient.

Finally it has been demonstrated that tablet formulations comprising the novel blends provide dissolution performance that is independent of pH, largely maintained following subdivision, and which can reduce the release rate of API in the presence of ethanol. Unlike film based ER dosage form technologies which may dose dump under these conditions, the novel blended controlled-release modifying release excipient provides an extra level of protection to the patient and peace of mind to the healthcare provider.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

1. Dumoulin Y. U.S. Pat. No. 5,807,575
2. Lenaerts V. U.S. Pat. No. 6,607,748 B1
3. Moore, J. W. and H. H. Flanner, 1996, "Mathematical Comparison of Dissolution Profiles," Pharmaceutical Technology, 20 (6):64-74.
4. Tramadol hydrochloride. Full Prescribing information https://www.accessdata.fda.gov/drugsatfda_docs/label/2009/020281s032s0331lbl.pdf
5. Acetaminophen Dosage https://www.drugs.com/dosage/acetaminophen.html
6. deVane C. J Clin Psychiatry. 2003; 64 Suppl. 18:14-9
7. Klein E. J Clin Psychiatry. 2002; 63 Suppl 14:27-33.
8. Michelson E. Clin Cardiol. 1991 December; 14(12):947-50.
9. Nicholson B. Pain Pract. 2009 January-February; 9(1):71-81
10. Navarro V. Adv Ther. 2010 November; 27(11):785-95.
11. Porter C. Drug Development and Industrial Pharmacy Volume 15, 1989-Issue 10
12. Thakral S. Expert Opinion on Drug Delivery Volume 10, 2013—Issue 1
13. Rosiaux Y J. Control Release. 2013 Jul. 10; 169(1-2):1-9.
14. Bhardway T. Drug Development and Industrial Pharmacy Volume 26, 2000-Issue 10
16. Singh K. Journal of Drug Delivery & Therapeutics; 2013, 3(5), 156-162
17. Hiremath P. AAPS PharmSciTech. 2008; 9(4):1171-1178.
18. U.S. Pat. No. 8,414,919.

All references referred to herein are incorporated by reference in their entireties.

What is claimed is:

1. A modified release pharmaceutical dosage form comprising:
   a CNS active drug, and a release modifying excipient, the release modifying excipient comprising:
   70-80% (wt/wt) of a non-cross-linked high amylose starch,
   10-20% (wt/wt) of a cross-linked hydroxypropylated amylopectin, and
   5-15% (wt/wt) of a pre-gelatinized common starch,
   wherein the modified release pharmaceutical dosage form is breakable into two or more pieces.

2. The modified release pharmaceutical dosage form of claim 1, wherein the CNS active drug comprises an analgesic, an antidepressant, or an anxiolytic drug.

3. The modified release pharmaceutical dosage form of claim 1, wherein the CNS active drug comprises tramadol hydrochloride, trazodone hydrochloride, or a pharmaceutically acceptable salts thereof.

4. The modified release pharmaceutical dosage form of claim 3, wherein the CNS active drug comprises the tramadol hydrochloride or the pharmaceutically acceptable salt thereof.

5. The modified release pharmaceutical dosage form of claim 4, which is scored.

6. The modified release pharmaceutical dosage form of claim 4, which, upon subdivision, maintains substantially the same release profile for the tramadol or the pharmaceutically acceptable salt thereof as the intact dosage form.

7. The modified release pharmaceutical dosage form of claim 4, which comprises the tramadol or the pharmaceutically acceptable salt thereof in an amount of 50 mg, or 100 mg, or 150 mg, or 200 mg, or 300 mg.

8. The modified release pharmaceutical dosage form of claim 4, comprising 13 to 56% (wt/wt) of the tramadol or the pharmaceutically acceptable salt thereof, and 5 to 20% (wt/wt) combined weight of the high amylose starch, the cross-linked hydroxypropylated amylopectin, and the pre-gelatinized common starch.

9. The modified release pharmaceutical dosage form of claim 4, wherein, upon subdivision, the two subdivided portions release less than 50% of the tramadol or the pharmaceutically acceptable salt thereof at four hours, as measured in a USP Type III Apparatus in 900 mL of pH 6.8 phosphate buffer at 100 rpm at a temperature of 37° C.

10. The modified release pharmaceutical dosage form of claim 3, wherein the CNS active drug comprises the trazodone hydrochloride or the pharmaceutically acceptable salt thereof.

11. The modified release pharmaceutical dosage form of claim 10, which is scored.

12. The modified release pharmaceutical dosage form of claim 10, which, upon subdivision, maintains substantially the same release profile for the tramadol or the pharmaceutically acceptable salt thereof as the intact dosage form.

13. The modified release pharmaceutical dosage form of claim 10, which comprises the trazadone or the pharmaceutically acceptable salt thereof in an amount of 75 mg, 150 mg or 300 mg.

14. The modified release pharmaceutical dosage form of claim 10, comprising 25 to 75% (wt/wt) of the trazodone or the pharmaceutically acceptable salt thereof, and 15 to 60% (wt/wt) combined weight of the high amylose starch, the cross-linked hydroxypropylated amylopectin, and the pre-gelatinized common starch.

15. The modified release pharmaceutical dosage form of claim 10, comprising 45 to 55% (wt/wt) of the trazodone or the pharmaceutically acceptable salt thereof, and 27 to 38% (wt/wt) combined weight of the high amylose starch, the cross-linked hydroxypropylated amylopectin, and the pre-gelatinized common starch.

16. The modified release pharmaceutical dosage form of claim 10, wherein, upon subdivision, the two subdivided portions release less than 50% of the trazodone or the pharmaceutically acceptable salt thereof at four hours, as measured in a USP Type III Apparatus in 900 mL of pH 6.8 phosphate buffer at 100 rpm at a temperature of 37° C.

* * * * *